US00PP24749P2

(12) United States Plant Patent
Davis

(10) Patent No.: US PP24,749 P2
(45) Date of Patent: Aug. 12, 2014

(54) ***NANDINA* PLANT NAMED 'LEMON-LIME'**

(50) Latin Name: *Nandina domestica*
Varietal Denomination: Lemon-Lime

(71) Applicant: Richard E. Davis, Locustville, VA (US)

(72) Inventor: Richard E. Davis, Locustville, VA (US)

(73) Assignee: Plants Nouveau, LLC, Charleston, SC (US)

( * ) Notice: Subject to any disclaimer, the term of this patent is extended or adjusted under 35 U.S.C. 154(b) by 42 days.

(21) Appl. No.: 13/694,874

(22) Filed: Jan. 14, 2013

(51) Int. Cl.
*A01H 5/00* (2006.01)

(52) U.S. Cl.
USPC ..... Plt./235

(58) Field of Classification Search
USPC ..... Plt./235, 226
See application file for complete search history.

*Primary Examiner* — Kent L Bell
(74) *Attorney, Agent, or Firm* — Penny J. Aguirre

(57) ABSTRACT

A new cultivar of *Nandina domestica* named 'Lemon-Lime', characterized by its short leaf internodes resulting in a very compact plant habit and its chartreuse new foliage and mature foliage on the outer regions of the plant that are exposed to bright sunlight with contrasting green foliage on the interior region of the plant that is shaded.

2 Drawing Sheets

Botanical classification: *Nandina domestica.*
Variety denomination: 'Lemon-Lime'.

BACKGROUND OF THE INVENTION

The present invention relates to a new and distinct cultivar of *Nandina domestica* and will be referred to hereafter by its cultivar name, 'Lemon-Lime'. 'Lemon-Lime' is a new cultivar of *Nandina* shrub grown for use as a landscape plant.

The new cultivar was discovered as a single unique plant by the Inventor in May of 2004 in Locustville, Va. The Inventor collected and sowed seeds from open-pollinated plants of *Nandina domestica* 'Aurea' (not patented) in December of 2002. The new cultivar was selected as a single unique plant from the resulting seedlings in 2004.

Asexual propagation of the new cultivar was first accomplished by the inventor using terminal stem cuttings in November of 2006 in Locustville, Va. Asexual propagation by softwood stem cutting and in vitro propagation has been determined that the characteristics of 'Lemon-Lime' are stable and reproduced true to type in successive generations.

SUMMARY OF THE INVENTION

The following traits have been repeatedly observed and represent the characteristics of the new cultivar as grown outdoors in trial beds and in containers in Locustville, Va. These attributes in combination distinguish 'Lemon-Lime' as a unique cultivar of *Nandina.*

1. 'Lemon-Lime' exhibits short leaf internodes resulting in a very compact plant habit.
2. 'Lemon-Lime' exhibits new leaves that are chartreuse in color and remain chartreuse in the outer regions of the plant that are exposed to bright sunlight above contrasting green foliage on the interior region of the plant that is shaded.
3. 'Lemon-Lime' typically does not bloom and only a few rare flowers have been observed.

'Aurea', the parent plant of 'Lemon-Lime' is similar to 'Lemon-Lime' in foliage coloration, however 'Aurea' differs from 'Lemon-Lime' in having a less compact plant habit and in producing flowers. 'Lemon-Lime' can be most closely compared to the cultivars 'Gulfstream' (U.S. Plant Pat. No. 5,656) and 'Compacta' (not patented). Both 'Gulfstream' and 'Compacta' are similar to 'Lemon-Lime' in having a compact plant habit. Both 'Gulfstream' and 'Compacta' differ from 'Lemon-Lime' in having foliage with new foliage that is red tinged and mature foliage that is green. 'Compacta' also differs from 'Lemon-Lime' in producing blooms and fruit.

BRIEF DESCRIPTION OF THE DRAWING

The accompanying colored photographs illustrate the overall appearance and distinct characteristics of three year-old plants of the new *Nandina* as grown outdoors in 3-gallon containers in Locustville, Va.

The photograph in FIG. 1 illustrates the overall appearance of 'Lemon-Lime'.

Figure 1:
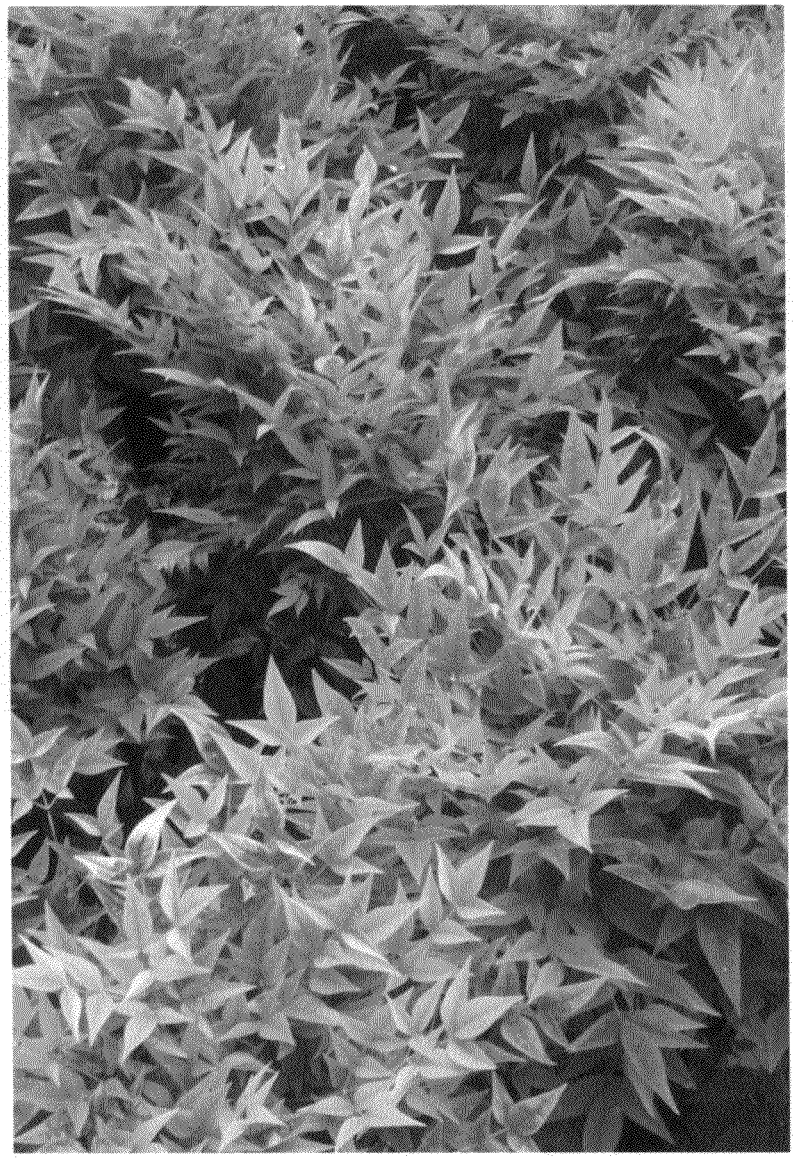
Figure 2:
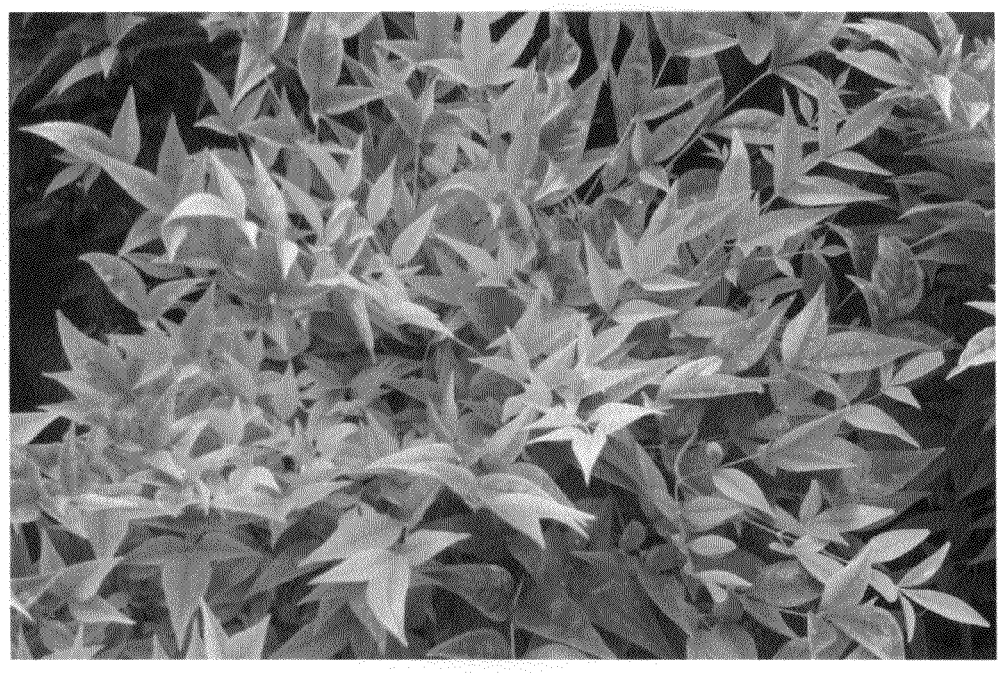

The photograph in FIG. 2 provides a close-up view of the foliage and plant habit of 'Lemon-Lime'.

The colors in the photographs are as close as possible with the digital photography techniques utilized and the color values cited in the detailed botanical description accurately describe the colors of the new *Nandina.*

DETAILED BOTANICAL DESCRIPTION

The following is a detailed description of 1 year-old plants of the new cultivar as grown outdoors in 2-liter containers in Locustville, Va. with additional information provided as observed on plants 6 years in age as grown in a trial bed in Locustville, Va. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen to semi-evergreen shrub.

*Plant habit.*—Compact, upright stem with dense foliage.

*Height and spread.*—Reaches about 36 inches in height and 42 inches in width after six years in the landscape, 1 year-old plants in a one-gallon container reach about 25 cm in height and 45 cm in width.

*Hardiness.*—At least in U.S.D.A. Zones 7 to 10.

*Diseases and pests.*—No particular resistance or susceptibility to diseases or pests has been observed.

*Root description.*—Fibrous, outward spreading by underground rhizomes has not been observed.

*Propagation.*—Basal stem cuttings and tissue culture.

*Growth rate.*—Moderate.

Stem description:

*Cane shape.*—Comprised of clasping petioles.

*Stem strength.*—Strong.

*Stem color.*—144A to 144B.

*Stem size.*—Average of 11 cm in length and 9 mm in width.

*Stem surface.*—Smooth.

*Stem aspect.*—Upright.

*Internode length.*—2 mm.

*Branching.*—Un-branched.

Foliage description:

*Leaf shape.*—Ovate overall.

*Leaf division.*—Tri-pinnate, with an average of 41 leaflets.

*Leaf arrangement.*—Alternate.

*Leaf attachment.*—Petiolate.

*Leaflet base.*—Cuneate.

*Leaflet apex.*—Attenuate.

*Leaflet fragrance.*—None.

*Leaflet venation.*—Pinnate, not conspicuous, matches leaf color on upper surface, mid rib is slightly protruding on lower surface.

*Leaflet margins.*—Entire.

*Leaflet surface.*—Glabrous on upper and lower surface.

*Leaf size.*—Average of 15 cm in length and 25 cm in width.

*Leaflet size.*—Average of 4 cm in length and 1.5 cm in width.

*Leaflet color.*—Newly expanded leaves and mature leaves in full sunlight upper surface; a blend of 1A with 145C near base and midrib, newly expanded leaves and mature leaves in full sunlight lower surface; a blend of 1B and 145C, leaves in shaded areas upper surface; 137B and aging to N137A, mature leaves lower surface; 138B and aging to 137D, fall color; not distinct, outer leaves 145C on upper surface and N137A on lower surface, inner leaves N137A on upper surface and 137D on lower surface.

*Petioles.*—Average of 25 cm in length and 2 mm in diameter, 144A to 144B in color, surface is glabrous and dull, clasping base 5 mm in width and length.

*Petiolules.*—Primary; average of 16 cm in length and 1.5 mm in width, 144A to 144B in color, surface is glabrous and dull, secondary; average of 10 cm in length and 1 mm in width, 144A to 144B in color, surface is glabrous and dull.

Inflorescence description: Blooms are very rare, typically plants of the new cultivar do not bloom, a few blooms were observed in June of 2010 however data was not collected.

It is claimed:

1. A new and distinct cultivar of *Nandina* plant named 'Lemon-Lime' as herein illustrated and described.

* * * * *